United States Patent [19]
Heitz et al.

[11] Patent Number: 5,733,959
[45] Date of Patent: Mar. 31, 1998

[54] STABILIZED POLYESTER MOLDING COMPOSITIONS

[75] Inventors: Thomas Heitz, Dannstadt-Schauernheim; Manfred Heym, Weisenheim; Klaus Mühlbach, Grünstadt; Christoph Plachetta, Limburgerhof, all of Germany

[73] Assignee: BASF Aktiengesellschaft, Ludwigshafen, Germany

[21] Appl. No.: 849,186

[22] PCT Filed: Nov. 21, 1995

[86] PCT No.: PCT/EP95/04577

§ 371 Date: May 30, 1997

§ 102(e) Date: May 30, 1997

[87] PCT Pub. No.: WO96/17011

PCT Pub. Date: Jun. 6, 1996

[30] Foreign Application Priority Data

Dec. 1, 1994 [DE] Germany .................. 44 42 724.7

[51] Int. Cl.$^6$ ................................................. C08K 5/29
[52] U.S. Cl. ................................................. 524/195
[58] Field of Search ............... 524/195; 528/80, 528/83; 560/84, 25, 27; 564/252

[56] References Cited

U.S. PATENT DOCUMENTS

| | | | |
|---|---|---|---|
| 3,776,882 | 12/1973 | Witzler et al. | 524/195 |
| 4,071,503 | 1/1978 | Thomas et al. | 525/440 |
| 4,987,168 | 1/1991 | Kerschbaumer | 524/195 |
| 5,210,170 | 5/1993 | Quiring et al. | 528/80 |
| 5,357,021 | 10/1994 | Tye et al. | 528/28 |
| 5,498,747 | 3/1996 | Pohl et al. | 524/195 |
| 5,504,241 | 4/1996 | Pohl et al. | 560/25 |
| 5,597,942 | 1/1997 | Pohl et al. | 560/25 |
| 5,621,031 | 4/1997 | Leimann et al. | 524/195 |

FOREIGN PATENT DOCUMENTS

| | | |
|---|---|---|
| 839 571 | 9/1976 | Belgium. |
| 460 481 | 12/1991 | European Pat. Off.. |
| 628 541 | 12/1994 | European Pat. Off.. |

Primary Examiner—Kriellion S. Morgan
Attorney, Agent, or Firm—Keil & Weinkauf

[57] ABSTRACT

Thermoplastic molding compositions comprise

A) from 20 to 99% by weight of a polyester, up to 90% by weight of which may be replaced by a polycarbonate or a polyamide, B) from 0.1 to 7% by weight of a carbodiimide of the formula I $$R^1-\underset{R^3}{\underset{|}{\overset{R^2}{\overset{|}{C}}}}-\underset{}{\overset{(R^4)_x}{\bigcirc}}-\underset{R^3}{\underset{|}{\overset{R^2}{\overset{|}{C}}}}-\left[N=C=N-\underset{R^3}{\underset{|}{\overset{R^2}{\overset{|}{C}}}}-\underset{}{\overset{(R^4)_x}{\bigcirc}}-\underset{R^3}{\underset{|}{\overset{R^2}{\overset{|}{C}}}}-\right]_n$$

$$-N=C=N-\underset{R^3}{\underset{|}{\overset{R^2}{\overset{|}{C}}}}-\underset{}{\overset{(R^4)_x}{\bigcirc}}-\underset{R^3}{\underset{|}{\overset{R^2}{\overset{|}{C}}}}-R^1 \quad \text{I,}$$

where
$R^1$ are identical or different radicals selected from the group consisting of —NCO, —NHCONHR$^5$, —NHCONR$^5$R$^6$ and —NHCOOR$^7$, where
$R^5$, $R^6$ are identical or different and are alkyl, cycloalkyl or aralkyl,
$R^7$ is the same as $R^5$ or is alkoxy(poly)oxyalkylene and
$R^2$, $R^3$ are identical or different aliphatic radicals having from 1 to 18 carbon atoms or cycloaliphatic radicals having from 5 to 15 carbon atoms or aromatic radicals having from 6 to 15 carbon atoms,
$R^4$ are identical or different aliphatic radicals having from 2 to 20 carbon atoms or halogen or alkoxy,
$x$ is an integer from 0 to 4 and
$n$ is an integer from 0 to 10, C) from 0 to 75% by weight of conventional additives and processing aids,
where the sum of the percentages by weight of components A) to C) is 100%.

8 Claims, No Drawings

STABILIZED POLYESTER MOLDING COMPOSITIONS

This application is a 371 of PCT/EP95/04577 filed Nov. 21, 1995.

The invention relates to thermoplastic molding compositions comprising

A) from 20 to 99% by weight of a polyester, up to 90% by weight of which may be replaced by a polycarbonate or a polyamide, B) from 0.1 to 7% by weight of a carbodiimide of the formula I

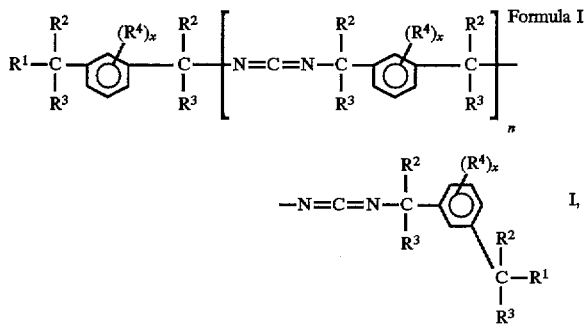

where
$R^1$ are identical or different radicals selected from the group consisting of —NCO, —NHCONHR$^5$, —NHCONR$^5$R$^6$ and —NHCOOR$^7$, where
$R^5$, $R^6$ are identical or different and are alkyl, cycloalkyl or aralkyl,
$R^7$ is the same as $R^5$ or is alkoxy(poly)oxyalkylene and
$R^2$, $R^3$ are identical or different aliphatic radicals having from 1 to 18 carbon atoms or cycloaliphatic radicals having from 5 to 15 carbon atoms or aromatic radicals having from 6 to 15 carbon atoms,
$R^4$ are identical or different aliphatic radicals having from 2 to 20 carbon atoms or halogen or alkoxy,
x is an integer from 0 to 4 and
n is an integer from 0 to 10, C) from 0 to 75% by weight of conventional additives and processing aids,
where the sum of the percentages by weight of components A) to C) is 100%.

The invention further relates to a method of using the novel molding compositions for producing shaped articles of any type, and to the shaped articles thus obtained.

It is known that polyesters may be protected against decomposition resulting from light or heat by adding organophosphorus compounds, phenolic antioxidants or aliphatic and/or aromatic amines.

U.S. Pat. No. 4,110,302 describes glass-fiber-reinforced mixtures of PBT with an aromatic polycarbodiimide, having improved impact strength. In Example 1, polytolylcarbodiimide is used.

U.S. Pat. No. 4,071,503 discloses mixtures of PBT with an aromatic polycarbodiimide having improved melt strength and solution viscosity. In the example which is given, polytolylcarbodiimide is used.

DE-A 41 08 278 describes PBT for producing fibers with improved thermal and hydrolytic stability, which is stabilized with mono- and/or bifunctional carbodiimides, and also, in the example, with a commercially-available aromatic polycarbodiimide having isopropyl groups on the benzene ring in the ortho position to the carbodiimide group.

BE-A 839 571 describes PBT which has improved melt strength for applications in extrusion and blow molding and is modified with an aromatic polycarbodiimide. In the general description, polycarbodiimides based on tolyl, biphenyl and diphenylmethane are described.

BE-A 846 445 describes fiber-reinforced mixtures according to BE-A 839 571 with improved impact strength for applications in extrusion and blow molding.

EP-A 898 213 describes blends of polyalkyl terephthalate and polycarbonate which are stable to hydrolysis and are stabilized with an aromatic polycarbodiimide of the structure:

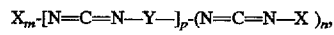

where X and Y are aliphatic or araliphatic groups in which at least one site in the ortho position to the carbodiimide group carries a substituent.

EP-A 46 04 81 discloses PBT with an aromatic polycarbodiimide according to EP-A 598 213 of the structure

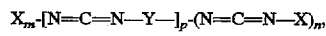

where X and Y are aliphatic or araliphatic groups in which at least one site in the ortho position to the carbodiimide group carries a substituent. In the example given, the polycarbodiimide from 1,3,5-triisopropylbenzene-2,4-diisocyanate is used.

JP-A 61/014 251 describes mixtures of PBT and copolymers of olefins with α,β-unsaturated acids with an aromatic polycarbodiimide. In Example 1, PET is used with addition of poly(1,6-hexamethylene)carbodiimide.

EP-A 411 339 describes copolyesters which contain a stabilizer mixture of a polyquinoline-based antioxidant and an aromatic polycarbodiimide and have improved aging resistance and melt viscosity. In Example 1, poly(1,4-phenylenecarbodiimide) is used.

In the prior art, all of the diamines which are employed in preparing the polycarbodiimides claimed have the amino group bonded in principle directly to an aromatic ring.

EP-A 94 108 216.6 proposes new carbodiimides and their use as stabilizers for polyurethanes.

A disadvantage of polyester molding compositions modified with the polycarbodiimides described is an increased tendency to yellowing, arising from the high aromatic content of the polycarbodiimide. The extreme steric hindrance of the aromatic rings at the carbodiimide group means that it is not possible to control a tendency to liberate isocyanate during processing at elevated temperatures, so that the processing of the polycarbodiimides described gives rise to toxicological hazards. Furthermore, the resistance of the known molding compositions to hydrolysis, especially by alkaline media, is unsatisfactory.

It is an object of the present invention to provide polyester molding compositions with improved resistance to hydrolysis, especially by alkaline media. They should have a very low tendency to yellowing, and the formation of mold deposit (monomeric carbodiimides) and the evolution of isocyanate (oligomeric carbodiimides) should be minimized during processing.

We have found that this object is achieved by the molding compositions defined at the outset. Preferred embodiments are seen in the subclaims.

The novel molding compositions contain, as component (A), from 20 to 99% by weight, preferably from 35 to 99% by weight, and in particular from 45 to 98.5% by weight, of a thermoplastic polyester.

Polyesters which are used are generally based on aromatic dicarboxylic acids and an aliphatic or aromatic dihydroxy compound.

A first group of preferred polyesters consists of polyalkylene terephthalates having from 2 to 10 carbon atoms in the alcohol moiety.

Polyalkylene terephthalates of this type are known per se and are described in the literature. They contain, in their main chain, an aromatic ring which derives from the aromatic dicarboxylic acid. The aromatic ring may also be substituted, for example with halogen, such as chlorine or bromine, or with $C_1$–$C_4$-alkyl, such as methyl, ethyl, isopropyl, n-propyl, n-butyl, isobutyl or tert-butyl.

These polyalkylene terephthalates can be prepared by reaction of aromatic dicarboxylic acids, their esters or other ester-forming derivatives with aliphatic dihydroxy compounds, in a manner known per se.

Preferred dicarboxylic acids are, for example, 2,6-naphthalene-dicarboxylic acid, terephthalic acid and isophthalic acid or mixtures of these. Up to 30 mol%, preferably not more than 10 mol%, of the aromatic dicarboxylic acids may be replaced by aliphatic or cycloaliphatic dicarboxylic acids, such as adipic acid, azelaic acid, sebacic acid, dodecanedioic acids or cyclohexanedicarboxylic acids.

Preferred aliphatic dihydroxy compounds are diols with from 2 to 6 carbon atoms, in particular 1,2-ethanediol, 1,4-butanediol, 1,6-hexanediol, 1,4-hexanediol, 1,4-cyclohexanediol, 1,4-cyclohexanedimethylanol, neopentyl glycol, and mixtures of these.

Particularly preferred polyesters (A) are, for example, polyalkylene terephthalates derived from alkanediols having from 2 to 6 carbon atoms. Of these, particular preference is given to polyethylene terephthalate and polybutylene terephthalate.

The relative viscosity of the polyesters (A) is in general in the range from 1.2 to 1.8 (measured in 0.5% strength by weight solution in a phenol/o-dichlorobenzene mixture (weight ratio 1:1) at 25° C.

A further group which may be mentioned is that of the fully aromatic polyesters derived from aromatic dicarboxylic acids and aromatic dihydroxy compounds.

Suitable aromatic dicarboxylic acids are the compounds described above in relation to polyalkylene terephthalates. Preference is given to mixtures of from 5 to 100 mol% of isophthalic acid and from 0 to 95 mol% of terephthalic acid, in particular mixtures of from about 80 to about 50% of terephthalic acid with about 20 to about 50% of isophthalic acid.

The aromatic dihydroxy compounds preferably have the formula IV

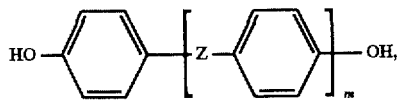

where Z is alkylene or cycloalkylene having up to 8 carbon atoms, arylene having up to 12 carbon atoms, carbonyl, sulfonyl, an oxygen or sulfur atom, or a chemical bond, and where m is from 0 to 2. Compounds IV may also carry $C_1$–$C_6$-alkyl or -alkoxy and fluorine, chlorine or bromine as substituents on the phenylene groups.

Representative compounds are, for example,
dihydroxydiphenyl,
di(hydroxyphenyl)alkane,
di(hydroxyphenyl)cycloalkane,
di(hydroxyphenyl) sulfide,
di(hydroxyphenyl) ether,
di(hydroxyphenyl) ketone,
di(hydroxyphenyl) sulfoxide,
α,α'-di(hydroxyphenyl)dialkylbenzene,
di(hydroxyphenyl) sulfone, di(hydroxybenzoyl)benzene, resorcinol and
hydroquinone and their ring-alkylated and ring-halogenated derivatives.

Of these, preferred compounds are
4,4'-dihydroxydiphenyl,
2,4-di(4'-hydroxyphenyl)-2-methylbutane,
α,α'-di(4-hydroxyphenyl)-p-diisopropylbenzene,
2,2-di(3'-methyl-4'-hydroxyphenyl)propane and
2,2-di(3'-chloro-4'-hydroxyphenyl)propane,
and in particular
2,2-di(4'-hydroxyphenyl)propane,
2,2-di(3',5-dichlorodihydroxyphenyl)propane,
1,1-di(4'-hydroxyphenyl)cyclohexane,
3,4'-dihydroxybenzophenone,
4,4'-dihydroxydiphenyl sulfone and
2,2-di(3',5'-dimethyl-4'-hydroxyphenyl)propane and mixtures of these.

It is also possible, of course, to employ mixtures of polyalkylene terephthalates and fully aromatic polyesters. These generally include from 20 to 98% by weight of the polyalkylene terephthalate and from 2 to 80% by weight of the fully aromatic polyester.

For the purposes of the present invention, polyesters also include polycarbonates which can be obtained by polymerization of aromatic dihydroxy compounds, in particular 2,2-bis(4-hydroxy-phenyl)propane (bisphenol A) and its derivatives, for example with phosgene. Products of this type are known per se and are described in the literature, and are mostly also commercially available. The amount of the polycarbonates is up to 90% by weight, preferably up to 50% by weight, based on 100% by weight of component (A).

Polyester block copolymers, such as copolyether esters, may, of course, also be used. Products of this type are known per se and are described in the literature, for example in U.S. Pat. No. 3,651,014. Corresponding products are also commercially available, for example Hytrel® (DuPont).

Furthermore, up to 90% by weight, preferably up to 50% by weight, in particular up to 30% by weight, of the polyester A) may be replaced by a polyamide, which may be either a partially crystalline or an amorphous polyamide. The components in the structure of polyamides, and processes for the preparation of polyamides, are known to the person skilled in the art, so that no details need be given here. Suitable polyamides are, for example, commercially available from BASF AG under the trademark Ultramid®.

The novel molding compositions contain, as component B), from 0.1 to 7% by weight, preferably from 0.5 to 5% by weight, and in particular from 1.5 to 3% by weight, of a carbodiimide of the formula I

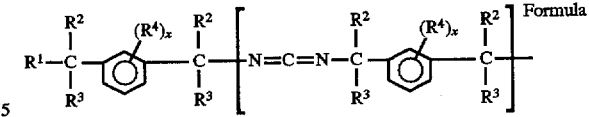

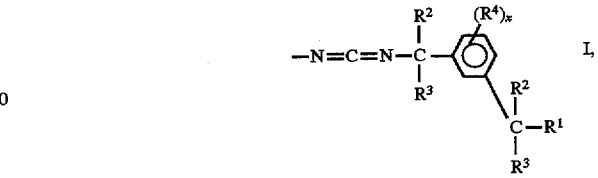

where $R^1$ are identical or different radicals selected from the group consisting of —NCO, —NHCONHR$^5$, —NHCONR$^5$R$^6$ and —NHCOOR$^7$, where R⁵, R⁶ are identical or different and are alkyl, cycloalkyl or aralkyl, R⁷ is the same as R⁵ or is alkoxy(poly)oxyalkylene and R², R³ are identical or different aliphatic radicals having from 1 to 18 carbon atoms or cycloaliphatic radicals having from 5 to 15 carbon atoms or aromatic radicals having from 6 to 15 carbon atoms, R⁴ are identical or different aliphatic radicals having from 2 to 20 carbon atoms or halogen or alkoxy x is an integer from 0 to 4 and n is an integer from 0 to 10.

Preferred aliphatic radicals R² and R³ are methyl, isopropyl, 2-methylpropyl and 2-methylhexyl, and methyl is particularly preferred.

Preferred cycloaliphatic radicals R², R³ are cyclobutyl, cyclohexyl and cycloundecyl, and cyclohexyl is particularly preferred.

Examples of aromatic radicals R², R³ are: phenyl, naphthyl, 2-tolyl and isopropylphenyl.

Examples of aliphatic radicals R⁴ are methyl, isopropyl and 2-methylpropyl, where x is an integer from 0 to 4, preferably 0 or 1.

Preference is given to carbodiimides and/or oligomeric polycarbodiimides of the formula (II)

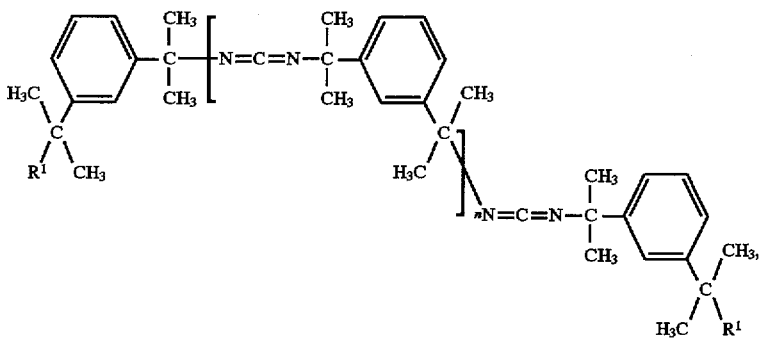

(II)

where

R¹ are identical or different radicals selected from the group consisting of —NCO, —NHCONHR⁵, —NHCONR⁵R⁶ and —NHCOOR⁷, where R⁵ and R⁶ are identical or different and are alkyl, cycloalkyl or aralkyl, and R⁷ is the same as R⁵ or is alkoxy(poly)oxyalkylene and n is an integer from 0 to 10.

The carbodiimides and oligomeric polycarbodiimides according to the invention have sterically hindered isocyanate, urea and/or urethane groups bonded to a methylene group; their efficacy in preventing hydrolysis is at least comparable with that of aromatic carbodiimides and aromatic polycarbodiimides which are used in industry, they have increased light stability, and they can be added cost- effectively without difficulty, without contravening safety-at-work regulations, and without additional homogenization steps, and incorporated into the ester-group-containing polycondensation and polyaddition products. An additional advantage is their large number of active carbodiimide groups relative to the molecular weight of the (poly) carbodiimides, their low vapor pressure, and their negligible tendency to migrate and bleed. The (poly)carbodiimides have good compatibility with the ester-group-containing polyesters, and because of their low melting point can also easily be mixed homogeneously with these materials in the melt.

The carbodiimides and oligomeric polycarbodiimides according to the invention, when reacted with carboxylic acids and/or carboxyl-containing compounds, give araliphatic isocyanates whose reactivity is low in comparison with that of aromatic isocyanates. As a result, the molecular weights of the resultant polyurethanes, and therefore also their mechanical properties, are constant and very easily reproducible. A further advantage is that the decomposition products arising from the isocyanates contain no aromatic amine groups and therefore pose few toxicological problems.

Besides the monomeric carbodiimides, use may be made of oligomeric polycarbodiimides, advantageously those having an average degree of condensation (number average) of from 2 to 10, preferably from 2 to 5, or mixtures of these, or mixtures of monomeric and oligomeric polycarbodiimides, since these are generally particularly easy to introduce into component A), which contains the ester groups to be stabilized. Polycarbodiimides having a higher degree of condensation are generally solid compounds with high melting points which are insufficiently compatible with the plastic matrix and therefore more difficult to mix homogeneously with the polyaddition or polycondensation products.

Particular preference is given to carbodiimides and/or oligomeric polycarbodiimides of the formula (III),

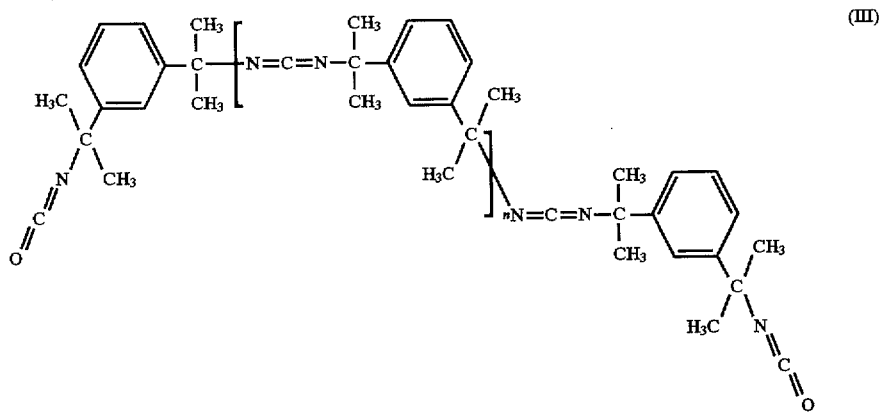

(III)

which retain reactive isocyanate groups and can therefore react with compounds having NCO-reactive hydrogen, and thus become chemically bonded in the polyaddition or polycondensation products. To improve the shelf life of the (poly)carbodiimides, some or all of the terminal isocyanate groups may be capped, for example, with compounds having reactive C—H or N—H, such as malonates, acetylacetone, acetoacetates, phthalimide, caprolactam or benzenesulfonamide, or deactivated using aliphatic, cycloaliphatic or araliphatic amines, alcohols or polyoxyalkylene alcohols, so that the physical properties of the (poly)carbodiimides, eg. their solubility or compatibility, are modified as required.

The deactivation of the isocyanate groups of the (poly)carbodiimides may, as already explained, be carried out using amines, alcohols or polyoxyalkylene alcohols. Suitable amines, eg. primary or preferably secondary amines, have advantageously from 1 to 12 carbon atoms, preferably from 2 to 8 carbon atoms. Examples are methylamine, ethylamine, propylamine, butylamine, pentylamine, hexylamine, 2-ethylhexylamine, octylamine, decylamine, diethylamine, dipropylamine, dibutylamine, methylbutylamine, ethylbutylamine, ethylhexylamine, cyclohexylamine and benzylamine. Deactivation of the isocyanate groups is, however, preferably carried out using alcohols, eg. primary or secondary alcohols having from 1 to 18 carbon atoms, preferably from 2 to 8 carbon atoms, and in particular alkoxypolyoxyalkylene alcohols having from 1 to 10 carbon atoms, preferably from 1 to 4 carbon atoms, in the alkoxy group and a molecular weight of from 76 to 2000, preferably from 400 to 1000 (number average). Examples of primary and secondary alcohols are methanol, ethanol, n-propanol, isopropanol, n-butanol, sec.-butanol, n-pentanol, technical pentanol mixtures, n-hexanol, technical hexanol mixtures, 2-ethylhexanol, octanol, 2-ethyloctanol, decanol, dodecanol, cyclohexanol and benzyl alcohol. Suitable alkoxy(poly)oxyalkylene alcohols are polyoxybutylene alcohols, polyoxypropylene alcohols, polyoxypropylene-polyoxyethylene alcohols and preferably polyoxyethylene alcohols, which may have, for example, methoxy, ethoxy, n-propoxy, isopropoxy or n-butoxy as terminal alkoxy group. Depending on the type of (poly)oxyalkylene radical used, the character of the (poly)carbodiimides may be adjusted in the range from hydrophilic, water-soluble, to hydrophobic, fat-soluble.

To prepare the carbodiimides and/or oligomeric polycarbodiimides according to the invention, 1,3-bis(1-methyl-1-isocyanatoethyl)-benzene may be condensed with elimination of carbon dioxide at elevated temperatures, eg. at from 50° to 200° C., preferably from 150° to 185° C., and expediently in the presence of catalysts. Suitable processes for this are described, for example, in GB-A-1 083 410, DE-B 1 130 594 (GB-A-851 936) and DE-A-11 56 401 (U.S. Pat. No. 3,502,722). Catalysts which have proven to be excellent are, for example, phosphorus compounds, preferably selected from the group consisting of phospholenes, phospholene oxides, phospholanes and phospholane oxides. When the reaction mixture has the desired content of NCO groups, corresponding to a degree of condensation n of up to 10, the formation of polycarbodiimide is usually terminated by distilling off the catalysts under reduced pressure or deactivating them by addition of a deactivator such as phosphorus trichloride. Furthermore, the polycarbodiimides may be prepared in the absence of, or in the presence of, solvents which are inert under reaction conditions.

By appropriate choice of the reaction conditions, for example of the reaction temperature, the type and amount of catalyst, and the reaction time, a person skilled in the art is able to adjust the degree of condensation in the usual manner. The course of the reaction may be followed most easily by determining the NCO content. Other parameters, for example viscosity increase, deepening of color or evolution of carbon dioxide, may also be used to follow and control the reaction.

As already described, when the condensation is finished the free terminal isocyanate groups of the carbodiimide and/or of the oligomeric polycarbodiimides may be blocked using compounds having reactive C—H or N—H, or some or all of the isocyanate groups may be deactivated using aliphatic, cycloaliphatic and/or araliphatic amines, or corresponding alcohols and/or alkoxypolyoxyalkylene alcohols. In an advantageous embodiment, in order to deactivate all of the isocyanate groups, the aliphatic, cycloaliphatic or araliphatic amines, alcohols and/or alkoxypolyoxyalkylene alcohols are preferably added so that there is a small excess of —OH, —NHR and/or —NH$_2$ groups to NCO groups of the reaction mixture containing (poly)carbodiimides, allowed to react to completion, and then any unreacted amount is distilled off, preferably under reduced pressure.

In another version of the process, which is preferred, the (poly)carbodiimides according to the invention, some or all of whose isocyanate groups are deactivated, may be prepared by reacting firstly up to 50% by weight, preferably up to 23% by weight, of the isocycanate groups of the 1,3-bis(1-methyl-1-iso-cyanatoethyl)benzene with at least one aliphatic, cycloaliphatic or araliphatic amine, alcohol and/or alkoxypolyoxyalkylene alcohol, and then condensing some or all of the free isocyanate groups to carbodiimides and/or oligomeric polycarbodiimides in the presence of catalysts, with elimination of carbon dioxide.

The monocarbodiimides and/or oligomeric polycarbodiimides according to the invention have excellent suitability as acceptors for carboxyl-containing compounds, and are therefore preferably used as hydrolysis stabilizers for polyesters and/or polyester-containing blends.

The novel molding compositions may contain, as component C), from 0 to 75% by weight, preferably up to 60% by weight, and in particular up to 50% by weight, of conventional additives and processing aids.

Conventional additives C) are, for example, elastomeric polymers (often also referred to as impact modifiers, elastomers or rubbers) in amounts of up to 40% by weight, preferably up to 30% by weight.

These are generally copolymers, preferably built up from at least two of the following monomers: ethylene, propylene, butadiene, isobutene, isoprene, chloroprene, vinyl acetate, styrene, acrylonitrile and (meth)acrylates having from 1 to 18 carbon atoms in the alcohol component.

Polymers of this type are described, for example, in Houben-Weyl, Methoden der organischen Chemie, Vol. 14/1 (Georg-Thieme-Verlag, Stuttgart, 1961), pp. 392 to 406 and in the monograph by C. B. Bucknail, "Toughened Plastics" (Applied Science Publishers, London, 1977).

Some preferred types of such elastomers are listed below.

Preferred types of such elastomers are the ethylene-propylene rubbers (EPM) and the ethylene-propylene-diene rubbers (EPDM).

EPM rubbers generally have virtually no residual double bonds, whereas EPDM rubbers may have from 1 to 20 double bonds per 100 carbon atoms.

Examples of diene monomers for EPDM rubbers are conjugated dienes, such as isoprene and butadiene, non-conjugated dienes with from 5 to 25 carbon atoms, such as penta-1,4-diene, hexa-1,4-diene, hexa-1,5-diene, 2,5-dimethylhexa-1,5-diene and octa-1,4-diene, cyclic dienes, such as cyclopentadiene, cyclohexadienes, cyclooctadienes and dicyclopentadiene, and alkenylnorbornenes, such as 5-ethylidene-2-norbornene, 5-butylidene-2-norbornene, 2-methallyl-5-norbornene, 2-isopropenyl-5-norbornene, and tricyclodienes, such as 3-methyltricyclo(5.2.1.0.2.6)-3,8-decadiene or mixtures of these. Preference is given to hexa-1,5-diene, 5-ethylidenenorbornene and dicyclopentadiene. The diene content of the EPDM rubbers is preferably from 0.5 to 50% by weight, in particular from 1 to 8% by weight, based on the total weight of the rubber.

EPM or EPDM rubbers may preferably also be grafted with reactive carboxylic acids or their derivatives, for example acrylic acid, methacrylic acid or their derivatives, such as glycidyl (meth)acrylate, or maleic anhydride.

Copolymers of ethylene with acrylic acid and/or methacrylic acid and/or the esters of these acids are a further group of preferred rubbers. The rubbers may also include dicarboxylic acids, such as maleic acid and fumaric acid, or derivatives of these acids, eg. esters or anhydrides, and/or epoxy-containing monomers. These dicarboxylic acid derivatives or epoxy-containing monomers are preferably incorporated into the rubber by addition to the monomer mixture of monomers containing dicarboxylic acid and/or epoxy groups of the formula I, II, III or IV:

$$R^1C(COOR^2)=C(COOR^3)R^4 \quad (I)$$

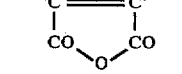

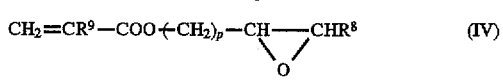

where $R^1$ to $R^9$ are hydrogen or alkyl having from 1 to 6 carbon atoms, and m is an integer from 0 to 20, g is an integer from 0 to 10, and p is an integer from 0 to 5.

$R^1$ to $R^9$ are preferably hydrogen, where m is 0 or 1 and g is 1. The corresponding compounds are maleic acid, fumaric acid, maleic anhydride, allyl glycidyl ether and vinyl glycidyl ether.

Preferred compounds of the formulae I, II and IV are maleic acid, maleic anhydride and epoxy-containing (meth)acrylates, such as glycidyl (meth)acrylate, and the esters with tertiary alcohols, such as tert-butyl acrylate. Although these latter have no free carboxyl groups, their behavior approximates to that of the free acids, and they are therefore referred to as monomers with latent carboxyl groups.

The copolymers advantageously consist of from 50 to 98% by weight of ethylene, from 0.1 to 20% by weight of epoxy-containing monomers and/or monomers containing methacrylic acid and/or anhydride groups, the residual amount being (meth)acrylates.

Particular preference is given to copolymers of
from 50 to 98% by weight, in particular from 55 to 95% by weight, of ethylene,
from 0.1 to 40% by weight, in particular from 0.3 to 20% by weight, of glycidyl acrylate and/or glycidyl methacrylate, (meth)acrylic acid and/or maleic anhydride, and
from 1 to 45% by weight, in particular from 10 to 40% by weight, of n-butyl acrylate and/or 2-ethylhexyl acrylate.

Other preferred acrylates and/or methacrylates are methyl, ethyl, propyl, isobutyl and tert-butyl (meth) acrylates.

Besides these, vinyl esters and vinyl ethers may be employed as comonomers.

The ethylene copolymers described above may be prepared by processes known per se, preferably by random copolymerization under elevated pressure and temperature. Processes of this type are well known.

Other preferred elastomers are emulsion polymers whose preparation is described, for example, by Blackley in the monograph "Emulsion Polymerization". The emulsifiers and catalysts which may be used are known per se.

In principle, both elastomers with a homogeneous construction and those with a shell construction may be employed. The shell construction depends on the addition sequence of the individual monomers; the morphology of the polymers is also influenced by this addition sequence.

Compounds which may be mentioned merely as examples of monomers for preparing the elastic part of the elastomers are acrylates, for example n-butyl acrylate and 2-ethylhexyl acrylate, the corresponding methacrylates, butadiene and isoprene and mixtures of these. These monomers may be copolymerized with other monomers, such as styrene, acrylonitrile, vinyl ethers and other acrylates or methacrylates, such as methyl methacrylate, methyl acrylate, ethyl acrylate and propyl acrylate.

The soft or elastic phase (with a glass transition temperature of less than 0° C.) of the elastomers can be the core, the outer shell or an intermediate shell (in elastomers of multishell construction); multishell elastomers may also have a number of shells formed from an elastic phase.

If one or more hard components (with glass transition temperatures of greater than 20° C.) are involved, besides the elastic phase, in the construction of the elastomer, these are generally prepared by polymerization of styrene, acrylonitrile, methacrylonitrile, α-methylstyrene, p-methylstyrene, or acrylates or methacrylates, such as methyl acrylate, ethyl acrylate and methyl methacrylate, as main monomers. Besides these, smaller amounts of other comonomers may also be employed.

In a number of cases, it has proven advantageous to employ emulsion polymers having reactive groups at the surface. Groups of this type are, for example, epoxy, carboxyl, latent carboxyl, amino and amido, and functional groups which can be introduced by incorporation of monomers of the formula

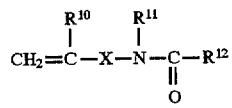

where
$R^{10}$ is hydrogen or $C_1$–$C_4$-alkyl,
$R^{11}$ is hydrogen, $C_1$–$C_8$-alkyl or aryl, in particular phenyl,
$R^{12}$ is hydrogen, $C_1$–$C_{10}$-alkyl, $C_6$–$C_{12}$-aryl or —$OR^{13}$,
$R^{13}$ is $C_1$–$C_8$-alkyl or $C_6$–$C_{12}$-aryl, each of which may be substituted with oxygen- or nitrogen-containing groups,
X is a chemical bond, $C_1$–$C_{10}$-alkylene or $C_6$–$C_{12}$-arylene or

Y is O—Z or NH—Z and
Z is $C_1$–$C_{10}$-alkylene or $C_6$–$C_{12}$-arylene.

The graft monomers described in EP-A 208 187 are also suitable for introducing reactive groups on the surface.

Further examples are acrylamide, methacrylamide and substituted acrylates and methacrylates, such as (N-tert-butylamino)ethyl methacrylate, (N,N-dimethylamino)ethyl acrylate, (N,N-dimethyl-amino)methyl acrylate and (N,N-diethylamino)ethyl acrylate.

The constituents of the elastic phase may also be crosslinked. Monomers which act as crosslinkers are, for example, buta-1,3-diene, divinylbenzene, diallyl phthalate, dihydro-dicyclopentadienyl acrylate and the compounds described in EP-A 50 265.

Use may, furthermore, be made of graft-linking monomers, ie. monomers having two or more polymerizable double bonds which react at different rates during polymerization. Preference is given to compounds of this type in which at least one reactive group polymerizes at about the same rate as the remaining monomers, whereas the other reactive group(s), for example, polymerize(s) significantly more slowly. The different polymerization rates give rise to a certain proportion of unsaturated double bonds in the elastomer. If a further phase is then grafted onto an elastomer of this type, at least some of the double bonds in the elastomer react with the graft monomers to form chemical bonds, ie. the grafted phase is, at least to some extent, linked to the graft base via chemical bonds.

Examples of such graft-linking monomers are allyl-containing monomers, in particular allyl esters of ethylenically unsaturated carboxylic acids, such as allyl acrylate, allyl methacrylate, diallyl maleate, diallyl fumarate, diallyl itaconate, and the corresponding monoallyl compounds of these dicarboxylic acids. In addition, there are many other suitable graft-linking monomers; further details may be seen, for example, in U.S. Pat. No. 4,148,846.

The proportion of these crosslinking monomers in the impact-modifying polymer is generally up to 5% by weight, preferably not more than 3% by weight, based on the impact-modifying polymer.

Some preferred emulsion polymers are listed below, beginning with graft polymers which have a core and at least one outer shell, and which have the following construction:

| Type | Monomers for the core | Monomers for the shell |
|---|---|---|
| I | Buta-1,3-diene, isoprene, n-butyl acrylate, ethylhexyl acrylate or mixtures of these | Styrene, acrylonitrile, methyl methacrylate |
| II | As I but with addition of crosslinkers | As I |
| III | As I or II | n-Butyl acrylate, ethyl acrylate, methyl acrylate, buta-1,3-diene, isoprene, ethylhexyl acrylate |
| IV | As I or II | As I or III but with addition of monomers with reactive groups as described herein |
| V | Styrene, acrylonitrile, methyl methacrylate or mixtures of these | First shell of monomers as described under I and II for the core Second shell as described under I or IV for the shell |

Instead of graft polymers with a multishell construction, homogeneous, ie. single-shell, elastomers of buta-1,3-diene, isoprene and n-butyl acrylate or copolymers of these may also be employed. These products may also be prepared with addition of crosslinking monomers or monomers with reactive groups.

Examples of preferred emulsion polymers are n-butyl acrylate-(meth)acrylate copolymers, n-butyl acrylate-glycidyl acrylate and n-butyl acrylate-glycidyl methacrylate copolymers, graft polymers with an inner core of n-butyl acrylate or based on butadiene and an outer shell of the abovementioned copolymers and copolymers of ethylene with comonomers which provide reactive groups.

The elastomers described may also be prepared by other conventional processes, for example by suspension polymerization.

Preference is likewise given to silicone rubbers, as described in DE-A 37 25 576, EP-A 235 690, DE-A 38 00 603 and EP-A 319 290.

Mixtures of the rubber types mentioned above may, of course, also be employed.

Examples of fibrous or particulate fillers are carbon fibers, glass fibers, glass beads, amorphous silica, asbestos, calcium silicate, calcium metasilicate, magnesium carbonate, kaolin, chalk, powdered quartz, mica, barium sulfate and feldspar, in amounts of up to 50% by weight, in particular up to 40% by weight.

The novel thermoplastic molding compositions may contain, as component C), conventional processing aids, such as stabilizers, oxidation inhibitors, thermal and UV stabilizers, lubricants, demolding aids, colorants, such as dyes and pigments, nucleating agents, plasticizers, etc.

Examples of oxidation inhibitors and thermal stabilizers are sterically hindered phenols, hydroquinones, aromatic secondary amines such as diphenylamines, and various substituted members of these groups, and mixtures of these in concentrations of up to 1% by weight, based on the weight of the thermoplastic molding composition.

Examples of UV stabilizers, generally used in amounts of up to 2% by weight, based on the molding composition, are various substituted resorcinols, salicylates, benzotriazoles and benzophenones.

Furthermore, organic dyes, such as nigrosin, and pigments, such as titanium dioxide, cadmium sulfide, cadmium selenide, phthalocyanine, ultramarine blue and carbon black, may be added as colorants.

Sodium phenylphosphinate, alumina, silica or, preferably, talc may be employed as nucleating agents.

Lubricants and demolding aids, which are usually employed in amounts of up to 1% by weight, are preferably long-chain fatty acids (eg. stearic acid and docosanoic acid), salts of these (eg. calcium and zinc stearates) or ester derivatives (eg. stearyl stearate or pentaerythrityl tetrastearate) or amide derivatives (eg. ethylenebisstearylamide).

Examples of plasticizers are dioctyl phthalate, dibenzyl phthalate, butyl benzyl phthalate, hydrocarbon oils and N-(n-butyl)benzenesulfonamide.

The novel molding compositions may also include from 0 to 2% by weight of fluorine-containing ethylenic polymers. These are ethylenic polymers with a fluorine content of from 55 to 76% by weight, preferably from 70 to 76% by weight.

Examples of these are polytetrafluoroethylene (PTFE), tetrafluoroethylene-hexafluoropropylene copolymers and tetrafluoroethylene copolymers with smaller proportions (generally up to 50% by weight) of copolymerizable ethylenically unsaturated monomers. These are described, for example, by Schildknecht in "Vinyl and Related Polymers", Wiley, 1952, pp. 484 to 494 and by Wall in "Fluoropolymers" (Wiley Interscience, 1972).

These fluorine-containing ethylenic polymers are homogeneously distributed in the molding compositions and preferably have a particle size $d_{50}$ (number average) in the range from 0.05 to 10 μm, in particular from 0.1 to 5 μm.

Examples of flame retardants are organic chlorine and bromine compounds, alkaline earth metal hydroxides, preferably with synergists, such as organophosphorus compounds and/or antimony trioxide and mixtures of carbonates of elements in the second main group of the Periodic Table and red phosphorus.

The novel thermoplastic molding compositions can be prepared by processes known per se, by mixing the starting components in conventional mixing apparatus such as screw-extruders, Brabender mixers or Banbury mixers, and then extruding them. After extrusion, the extrudate can be cooled and comminuted. It is also possible to premix individual components and then to add the remaining starting materials, either individually or likewise mixed. The mixing is generally carried out at from 230° to 290° C.

In a preferred method of operation, component B) and, if desired, conventional additives C) can be mixed with a polyester prepolymer, compounded and granulated. The resultant granules are then subjected to continuous or batch condensation in the solid phase under inert gas at a temperature below the melting point of component A), until the desired viscosity is reached.

The novel thermoplastic molding compositions have good stability to hydrolysis together with good dimensional stability. They are suitable for producing fibers, films and shaped articles, in particular for outdoor applications, in damp/humid conditions, or for applications involving contact with water.

EXAMPLES

The following components were used:

Component A): polybutylene terephthalate with a viscosity number of 127 ml/g (Ultradur®B 4520 from BASF AG, viscosity number measured in 0.5% strength by weight solution of phenol/o-dichlorobenzene, 1:1 mixture, at 25° C.).

Component B)

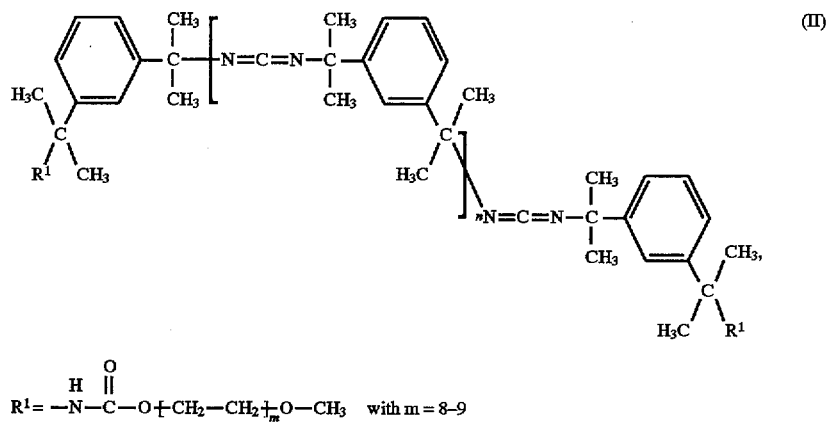

(Luprogen® VP 9238)

These low particle sizes may particularly preferably be achieved by the use of aqueous dispersions of fluorine-containing ethylenic polymers and by incorporating these into a polyester melt.

To improve compatibility with the thermoplastic polyester, minerals and fillers are, if desired, treated with a bonding agent. Glycidyl-, vinyl- and aminoalkyltrialkoxysilanes are preferred.

Examples 1 to 7 and Comparative Example 1

Components A) and B) were mixed in a twin-screw extruder (ZSK 30, Werner & Pfleiderer; rotational speed 200 rpm, throughput 10 kg/h) at 260° C., and extruded into a water bath. Test specimens were injection molded from the granulated and dried product.

The hydrolysis test specimens were stored for the stated time in water at a temperature of 100° C. in an autoclave under intrinsic pressure.

The mechanical properties were determined by the following methods:

Tensile test according to ISO 527-2 (on test specimen ISO 3167: 1993 Type 1A) with an extension rate of 5 mm/min (initial extension rate of 1 mm/min for determination of modulus of elasticity).

Flexural impact strength test (Charpy) according to ISO 179 on test specimen 1eU at 23° C.

Notched impact strength test according to ISO 179 at 23° C. on test specimen 1ea (S) with molded notch.

Melt flow index (MVI) at 250° C., with a melting time of 4 min and 2.16 kg load.

Solution viscosity at 25° C. in a 0.5% strength solution of PBT in a mixture of o-dichlorobenzene and phenol (1:1).

The results of the measurements and the formulations of the molding compositions are seen in Table 1.

Examples 8 to 13 and Comparative Example 2

Components A) and B) were compounded and granulated under conditions corresponding to Examples 1 to 7. The granules were then post-condensed (post-cured) in the solid phase in a tumbler drier at 205° C. for 24 hours under nitrogen, to give the viscosity numbers shown in Table 2.

The formulations of the molding compositions and the results of the measurements are seen in Table 2.

TABLE 1

| Example | Component B) [% by weight] | Puncture test ISO 6603-2 23° C. [Nm] | Impact strength ISO 179 1eU 23° C. [kJ/m²] | Notched impact strength ISO 179 1eA(S) 23° C. [kJ/m²] | Viscosity number after compounding 25° C. [ml/g] | MVI 250/ 2.16/4' [ml/10 min] |
|---|---|---|---|---|---|---|
| 1 | 0.2 | 42.9 | 267.0 | 5.3 | 136.0 | 21.1 |
| 2 | 0.5 | 41.1 | 269.9 | 5.4 | 139.0 | 19.2 |
| 3 | 1 | 41.7 | 262.8 | 5.4 | 142.0 | 15.0 |
| 4 | 1.5 | 42.1 | 268.1 | 5.5 | 146.0 | 14.3 |
| 5 | 2 | 41.9 | 268.0 | 5.7 | 143.0 | 15.0 |
| 6 | 2.3 | 40.1 | 262.6 | 5.7 | 138.0 | 18.0 |
| 7 | 2.5 | 40.7 | 270.0 | 5.8 | 142.0 | 16.4 |
| C1 | — | 39.5 | 254.5 | 4.9 | 127.0 | 26.4 |

| | Tensile test | | | Tensile test 1 day in water 100° C. | | | Tensile test 4 days in water 100° C. | | |
|---|---|---|---|---|---|---|---|---|---|
| Ex. | Modulus of elasticity [MPa] | Tension [MPa] | Elongation at break [%] | Modulus of elasticity [MPa] | Tension [MPa] | Elongation at break [%] | Modulus of elasticity [MPa] | Tension [MPa] | Elongation at break [%] |
| 1 | 2530 | 56.6 | 37.2 | 2720 | 22.3 | 46.9 | 2531 | 48.8 | 10.6 |
| 2 | 2464 | 56.1 | 87.8 | 2254 | 23.1 | 74.6 | 2291 | 34.2 | 31.1 |
| 3 | 2373 | 55.1 | 58.3 | 2241 | 31.3 | 76.4 | 2245 | 23.8 | 35.7 |
| 4 | 2266 | 53.1 | 183.0 | 2191 | 33.0 | 127.0 | 2227 | 18.0 | 73.9 |
| 5 | 2191 | 51.6 | 238.4 | 2064 | 35.2 | 145.0 | 2093 | 25.4 | 109.5 |
| 6 | 2145 | 50.9 | 232.5 | 2027 | 24.1 | 106.6 | 2084 | 18.3 | 69.3 |
| 7 | 2145 | 50.8 | 267.8 | 1996 | 33.3 | 184.5 | 2038 | 21.2 | 96.5 |
| C1 | 2455 | 51.4 | 30.7 | 2289 | 20.0 | 83.8 | 2310 | 51.0 | 19.4 |

| | Tensile test 10 days in water 100° C. | | | Impact strength 23° C. [kJ/m²] | Impact strength 1 day in water 23° C. [kJ/m²] | Impact strength 4 days in water 23° C. [kJ/m²] | Impact strength 10 days in water 23° C. [kJ/m²] |
|---|---|---|---|---|---|---|---|
| Ex. | Modulus of elasticity [MPa] | Tension [MPa] | Elongation at break [%] | | | | |
| 1 | 2254 | 50.7 | 3.6 | 267.0 | 165.6 | 166.1 | 97.9 |
| 2 | 2266 | 54.6 | 7.0 | 269.9 | 154.1 | 165.6 | 116.7 |
| 3 | 2234 | 54.9 | 12.3 | 252.8 | 158.5 | 161.5 | 133.7 |
| 4 | 2199 | 50.9 | 18.4 | 268.1 | 155.8 | 159.0 | 163.3 |
| 5 | 2164 | 49.2 | 19.9 | 268.0 | 153.7 | 150.1 | 156.3 |
| 6 | 2057 | 48.1 | 20.6 | 262.6 | 149.4 | 160.5 | 152.5 |
| 7 | 2047 | 51.7 | 19.3 | 270.0 | 161.5 | 162.0 | 156.0 |
| C1 | 2345 | 20.0 | 0.9 | 254.5 | 160.7 | 174.3 | 15.5 |

TABLE 2

| Example | Component B) [% by weight] | Impact strength ISO 179 1eU 23° C. [kJ/m²] | Notched impact strength ISO 179 1eA(S) 23° C. [kJ/m²] | Viscosity number 25° C. [ml/g] | MVI 250/2.16/4' [ml/10 min] |
|---|---|---|---|---|---|
| 8 | 0.2 | 279.3 | 5.8 | 164 | 7.5 |
| 9 | 0.5 | 279.9 | 5.7 | 156 | 8.1 |
| 10 | 1 | 2523.7 | 5.6 | 155 | 9.5 |
| 11 | 2 | 239.8 | 5.3 | 142 | 14.8 |
| 12 | 2.3 | 267.8 | 4.3 | 148 | 14.8 |
| 13 | 2.5 | 265.7 | 3.5 | 140 | 15.3 |
| C2 | — | 281.0 | 6.6 | 169 | 3.8 |

| | Tensile test | | | Tensile test 1 day in water 100° C. | | | Tensile test 4 days in water 100° C. | | |
|---|---|---|---|---|---|---|---|---|---|
| Ex. | Modulus of elasticity [MPa] | Tension [MPa] | Elongation at break [%] | Modulus of elasticity [MPa] | Tension [MPa] | Elongation at break [%] | Modulus of elasticity [MPa] | Tension [MPa] | Elongation at break [%] |
| 8 | 2565 | 39.1 | 171.3 | 2393 | 37.8 | 199.5 | 2448 | 23.8 | 54.9 |
| 9 | 2552 | 41.7 | 210.5 | 2388 | 33.9 | 130.3 | 2390 | 25.6 | 73.4 |
| 10 | 2518 | 37.3 | 124.9 | 2173 | 33.9 | 171.8 | 2168 | 30.9 | 134.5 |
| 11 | 2376 | 37.0 | 155.3 | 2108 | 37.1 | 234.3 | 2099 | 28.5 | 149.1 |
| 12 | 2375 | 38.6 | 201.4 | 2075 | 32.0 | 160.0 | 2034 | 24.7 | 69.0 |
| 13 | 2335 | 53.8 | 210.0 | 2099 | 29.5 | 95.2 | 2046 | 27.0 | 55.6 |
| C2 | 2562 | 37.9 | 90.1 | 2547 | 35.6 | 50.4 | 2480 | 34.0 | 31.8 |

| | Tensile test 10 days in water 100° C. | | | Impact strength 23° C. [kJ/m²] | Impact strength 1 day in water 23° C. [kJ/m²] | Impact strength 4 days in water 23° C. [kJ/m²] | Impact strength 10 days in water 23° C. [kJ/m²] |
|---|---|---|---|---|---|---|---|
| Ex. | Modulus of elasticity [MPa] | Tension [MPa] | Elongation at break [%] | | | | |
| 8 | 2370 | 45.3 | 2.4 | 279.3 | 219.9 | 209.7 | 50.6 |
| 9 | 2278 | 44.9 | 2.4 | 279.3 | 213.9 | 212.8 | 36.8 |
| 10 | 2095 | 43.6 | 2.9 | 253.7 | 205.2 | 206.2 | 56.9 |
| 11 | 2042 | 44.3 | 2.9 | 239.8 | 211.1 | 240.7 | 79.5 |
| 12 | 2018 | 47.5 | 4.7 | 267.8 | 213.2 | 207.5 | 115.2 |
| 13 | 2027 | 48.2 | 4.6 | 265.7 | 210.7 | 249.4 | 157.7 |
| C2 | 2428 | 29.5 | 1.3 | 281.0 | 271.1 | 269.3 | 11.8 |

We claim:

1. A thermoplastic molding composition comprising

A) from 20 to 99% by weight of a polyester, up to 90% by weight of which may be replaced by a polycarbonate or a polyamide, B) from 0.1 to 7% by weight of a carbodiimide of the formula I

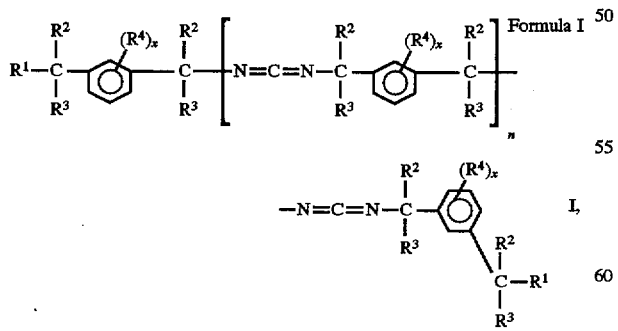

where

R$^1$ are identical or different radicals selected from the group consisting of —NCO, —NHCONHR$^5$, —NHCONR$^5$R$^6$ and —NHCOOR$^7$, where R$^5$, R$^6$ are identical or different and are alkyl, cycloalkyl or aralkyl, R$^7$ is the same as R$^5$ or is alkoxy(poly)oxyalkylene and R$^2$, R$^3$ are identical or different aliphatic radicals having from 1 to 18 carbon atoms or cycloaliphatic radicals having from 5 to 15 carbon atoms or aromatic radicals having from 6 to 15 carbon atoms, R$^4$ are identical or different aliphatic radicals having from 2 to 20 carbon atoms or halogen or alkoxy, X is an integer from 0 to 4 and n is an integer from 0 to 10, C) from 0 to 75% by weight of conventional additives and processing aids, where the sum of the percentages by weight of components A) to C) is 100%.

2. A thermoplastic molding composition as claimed in claim 1 wherein component A) is present in an amount of from 35 to 99.5% by weight and component B) is present in an amount of from 0.5 to 5% by weight.

3. A thermoplastic molding composition as claimed in claim 1 in which component B) is a carbodiimide of the formula II

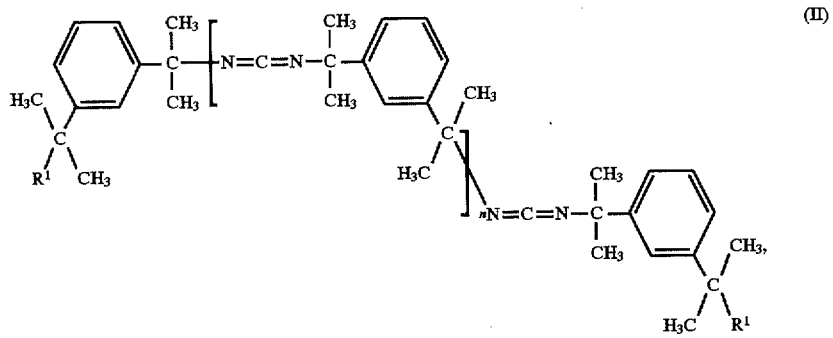

(II)

where

R¹ are identical or different radicals selected from the group consisting of —NCO, —NHCONHR⁵, —NHCONR⁵R⁶ and —NHCOOR⁷, where R⁵, R⁶ are identical or different and are alkyl, cycloalkyl or aralkyl, and R⁷ is the same as R⁵ or is alkoxy(poly)oxyalkylene and n is an integer from 0 to 10.

4. A thermoplastic molding composition as claimed in claim 1, containing, as component B), a carbodiimide and/or oligomeric polycarbodiimides of the formula (I), where R¹ is —NHCOOR⁷ and R⁷ is alkoxypolyoxyethylene with a molecular weight of from 76 to 2000 and n is an integer from 0 to 10.

5. A thermoplastic molding composition as claimed in claim 1, containing, as component B), a carbodiimide and/or oligomeric polycarbodiimides of the formula (III),

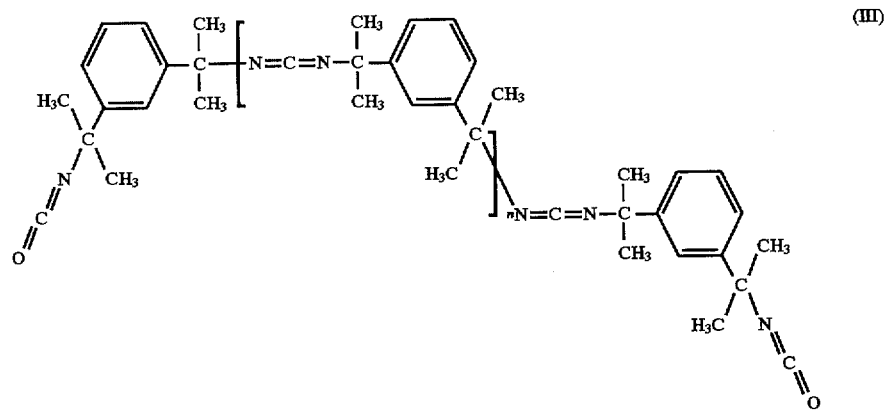

(III)

where n is an integer from 0 to 10.

6. A thermoplastic molding composition as claimed in claim 3, in which the carbodiimide of the formula II is obtainable a) by condensing 1,3-bis(1-methyl-1-isocyanatoethyl) benzene with elimination of carbon dioxide and, if desired, reacting some or all of the terminal isocyanate groups of the resultant carbodiimide and/or oligomeric polycarbodiimides with at least one aliphatic, cycloaliphatic or araliphatic amine, alcohol and/or alkoxypolyoxyalkylene alcohol or b) by reacting up to 50% of the isocyanate groups of the 1,3-bis(1-methyl-1-isocyanatoethyl)benzene with at least one aliphatic, cycloaliphatic or araliphatic amine, alcohol and/or alkoxypolyoxyalkylene alcohol, and then condensing the free isocyanate groups with elimination of carbon dioxide.

7. A thermoplastic molding composition as claimed in claim 5, in which the carbodiimide of the formula III is obtainable by condensation of 1,3-bis(1-isocyanatoethyl) benzene, with elimination of carbon dioxide.

8. A shaped article obtainable from the thermoplastic molding composition as claimed in any of claim 7.

* * * * *